United States Patent [19]

Bruinsma

[11] 4,044,595

[45] Aug. 30, 1977

[54] SHORT SPAN TENSILE TESTER SYSTEM

[76] Inventor: Bote G. Bruinsma, 2795 Bates Road, Montreal, Quebec, Canada

[21] Appl. No.: 706,923

[22] Filed: July 19, 1976

[51] Int. Cl.$^2$ .............................................. G01N 3/08
[52] U.S. Cl. ...................................................... 73/95
[58] Field of Search .......................... 73/95, 95.5, 103

[56] References Cited

U.S. PATENT DOCUMENTS

| 3,707,119 | 12/1972 | Cowan | 73/95 |
| 3,919,884 | 11/1975 | Gunderson et al. | 73/95 |

Primary Examiner—James J. Gill
Assistant Examiner—Anthony V. Ciarlante

[57] ABSTRACT

A short span tensile tester for testing a sheet such as a paper web is provided with two pairs of clamping jaws mounted in adjacent clamping relation, to clamp a portion of sheet material therebetween, one pair of jaws being pivotably mounted to swing under gravity into contacting relation with the other pair of jaws, to define a minimal span of up to about 3 m.m. A wedging device forces displacement of the jaws in the plane of the web to rupture the web, and force measuring means measure the wedge reaction force and hence the web rupture strength.

6 Claims, 3 Drawing Figures

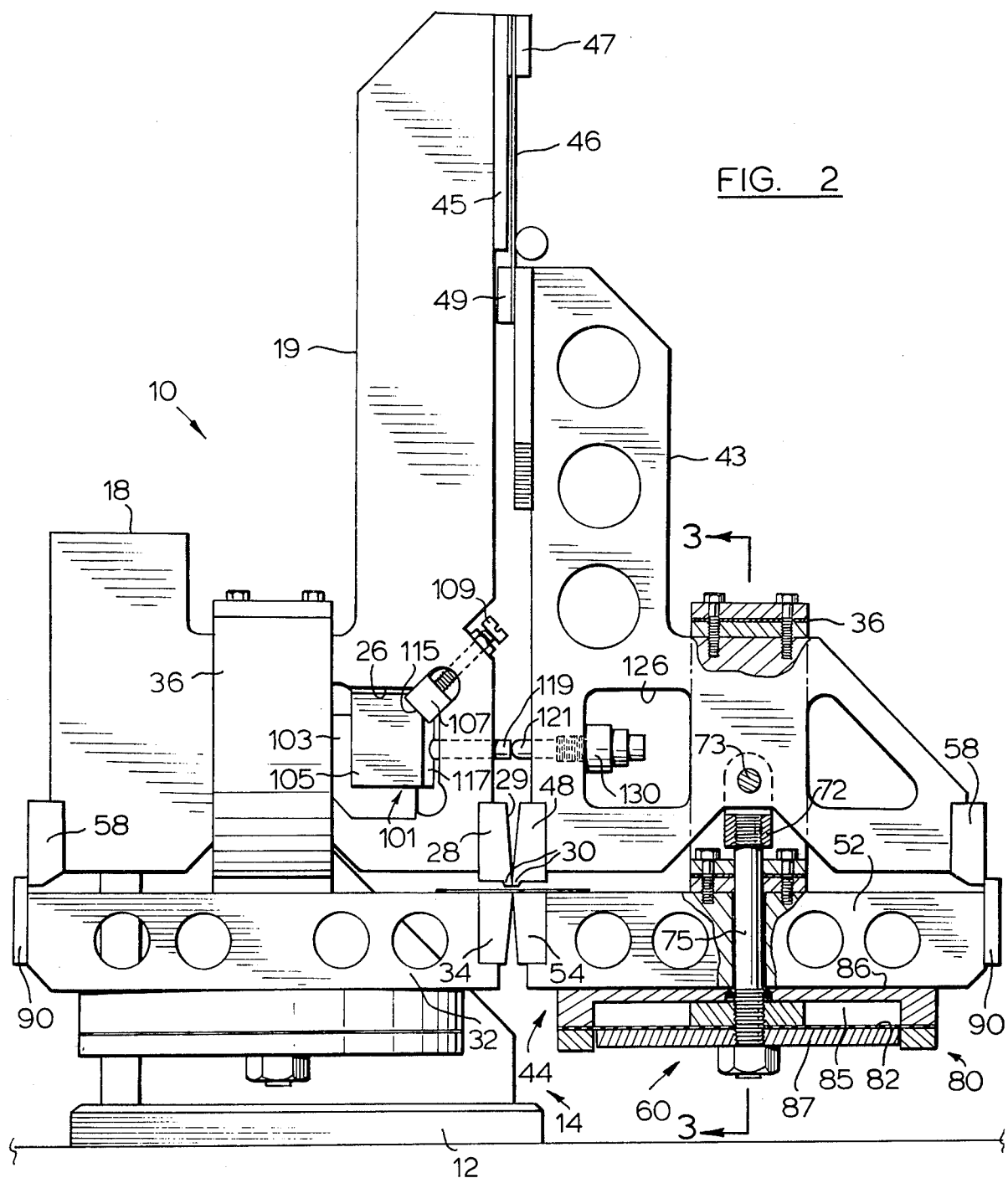

SHORT SPAN TENSILE TESTER SYSTEM

This invention is directed to a tensile testing device and in particular to a device for testing the rupture strength of a paper web over a minimal span.

In determination of the strength of the fibres embodied in a web of material such as paper, it is desireable to apply a rupturing force to a sample of the web, acting over a minimal gauge length, if the test is to give an indication of the strength of the fibres. Also, in order to achieve consistent results it is necessary to maintain alignment of the force acting on the web in the plane of the web, and to measure accurately the force necessary to produce rupture.

In an earlier arrangement in the name of Cowan, U.S. Pat. No. 3,707,119 Dec. 26, 1972, there is provided a zero gauge length tester having two pairs of opposed jaws, each with a pneumatic closer cylinder to grip a sheet of paper therebetween. One pair of jaws is supported from below in pivotal relation with the other pair of jaws. A pneumatic pusher mechanism secured to one pair of jaws is pressurised in pushing relation with the opposed set of jaws to separate the pairs of jaws one from the other substantially in the plane of the paper, thereby rupturing the paper.

The force applied by the pusher mechanism to provide failure of the paper sheet is a direct function of the tensile strength of the sheet.

This prior arrangement has certain limitations, particularly the time taken to mount the sheet sample therein, the functioning of the jaws in closing relation relying on lever arms, and the need to utilize a somewhat long paper sheet, of sufficient length to extend beyond ridges in a piston to prevent tilting of the sliding clamps.

Also, the mounting of the opposed jaw portions on slides permits wear of the sliding parts, leading ultimately to the possibility of misalignment of the jaws. The use of pneumatic direct jaw spreading results in constant force straining, which precludes obtaining desired graphic characteristics.

The present invention departs in certain significant aspects from the cited prior art, in the provision of underhung moveable jaws. Under the influence of gravity the underhung jaws can close together to provide a minimized "zero" gauge length. The use of cylindrical plate springs provides positioning of the underhung jaws with a single degree of freedom, and a wedge-like actuator is used to force the jaw sets apart to break the paper. Thirty microns is a typical stretch which is encountered in a typical paper web, tested over a "zero" span.

By selective initial wedge location the operator can choose the jaw spacing and hence the span he desires, and proceed to clamp and rupture the sheet. Full retraction of the wedge produces a "zero-span" condition when the two sets of jaws are in full contact to define a substantially zero gauge length.

Thus there is provided a tensile testing apparatus for testing the tensile strength of a web of sheet material, having two pairs of clamping jaws in adjacent clamping relation for clamping closely adjoining portions of the sheet material, wedging means to force one set of jaws away from the other set of jaws to produce rupturing of the web, and force measuring means to measure the applied rupture force. The apparatus further provides at least one pair of jaws having opposed first and second jaw portions with spring means extending therebetween in mutual positioning relation and having a single degree of freedom to permit closure of the jaws portions in accurately maintained coincidence.

Operation of the sets of jaws in clamping relation is provided by fluid inflatable clamping means located in direct load applying relation against the respective jaw mechanisms. In addition, the apparatus provides one set of jaws hanging in suspended relation adjacent the other set of jaws, having the centre of gravity of the suspended jaw set on the side of the plane of suspension remote from the plane of control with the other jaw set, to provide an eccentric load tending to maintain the two jaw sets in contact.

Certain embodiments of the present invention are described, reference being made to the accompanying drawings, wherein:

FIG. 2 is a side elevational view of the apparatus and;

Figure 1:
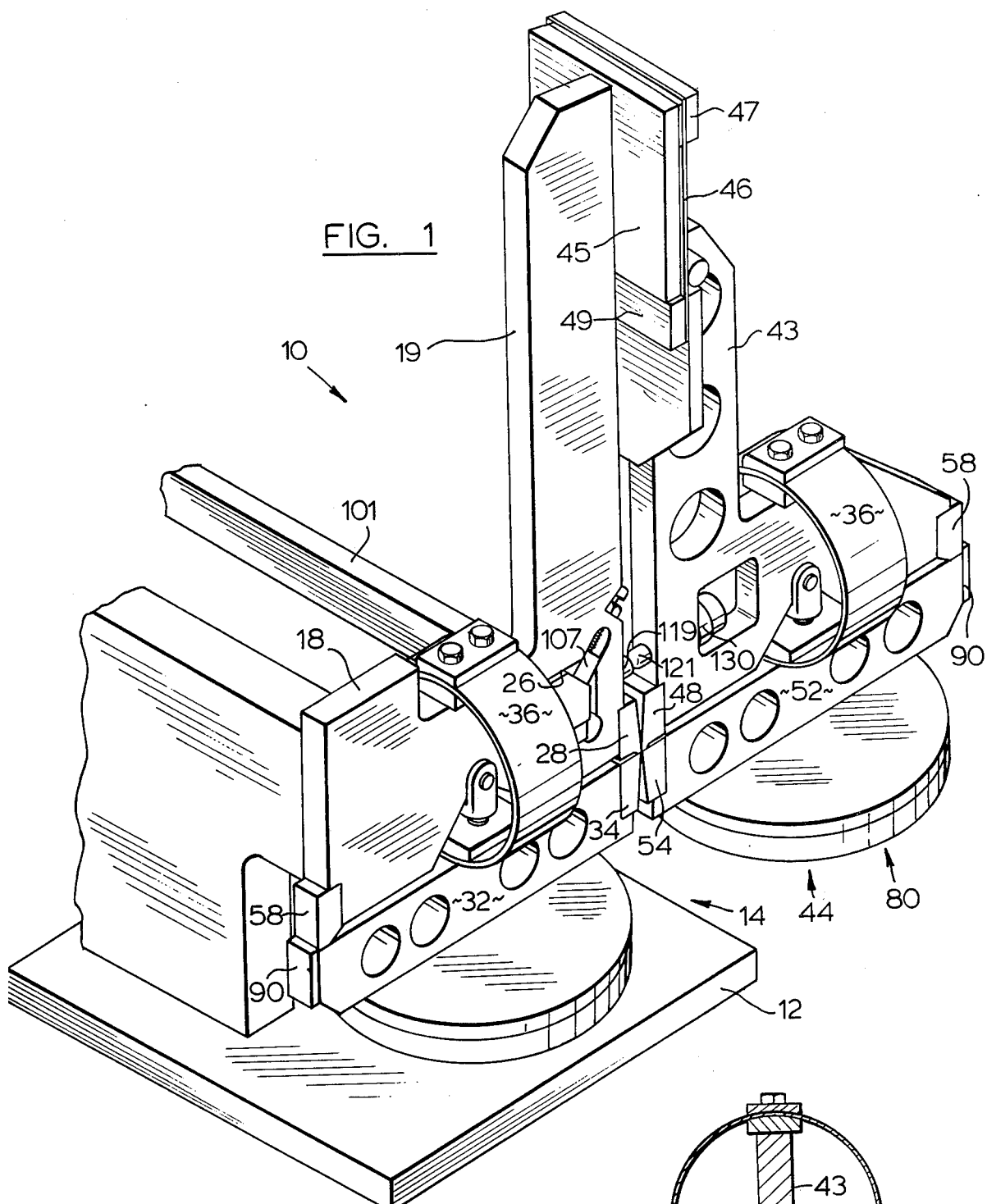
FIG. 1 is a general view of the subject web breaking apparatus.

Referring to FIGS. 1 and 2 of the drawings, the tester 10 has a base 12 on which the apparatus stands. A first clamp assembly 14 is cantilevered from the base 12. The clamp assembly 14 includes an L-shaped rib member 18 attached to the base 12 having an upstanding arm portion 19.

An aperture 26 in rib 18 serves as an actuator housing, referred to below.

A master jaw 28 is secured to the heel of the rib 18, the jaw 28 being provided with a relieved front face 29 terminating at its lower edge in a downwardly protruding pad portion 30, the frontal edge of which constitutes the master edge of the total clamp assembly, and defining both vertical and horizontal reference planes of the gripping point of the short span tester.

A lower beam 32 carries a lower jaw 34 in vertically aligned facing relation with the master jaw 28, being relieved vertically from the master edge. A cylindrical spring 36 extends in positioning relation between the rib 18 and the lower beam 32 in relation to jaw 28, so that precise registry of jaw 34 with jaw 28 is always maintained, in both the open and the closed condition.

The clamp actuating mechanism is similar for both clamp assemblies, and is described in detail below in relation to the moveable pair of jaws.

The moveable jaw assembly 44 is supported at its upper end by means of a resilient plate hinge 46 having the upper end thereof secured by a clamp plate 47 to a mounting plate 45 which is attached to the arm portion 19.

The centre of gravity of the assembly 44 lies to the right of the hinge plate 46, thereby producing a biassing gravitational moment which tends to bring the two clamp assemblies together in pressing relation, to define the "zero" gauge length.

The assembly 44 has an upper anvil jaw 48 similar in cross-section to the master jaw 28, as a mirror image thereof. The lower jaw 54 which corresponds with the lower jaw 34 is similarly mounted on a lower beam 52, secured by cylindrical spring 36 to the upper portion of the assembly 44.

The moveable jaw assembly 44 includes a generally L-shaped rib member 43, secured to the plate hinge 46 by a clamp plate 49.

Figure 3:
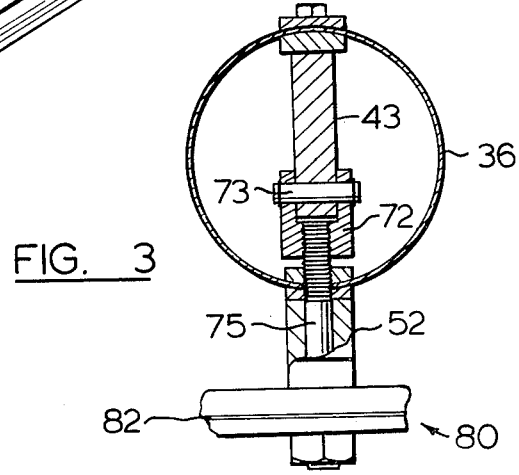
FIG. 3 is a view at 3—3 of FIG. 2.

The head portion 87 is carried in symetrically suspended relation by a clevis arrangement (FIG. 3) suspended from the rib member 43. A clevis fork 72 is secured by pivot pin 73 to the rib 43, the fork 72 having a threaded piston rod 75 extending downwardly therefrom. The rod 75 extends through an aperture in the lower beam 52 and extends into an air actuated servo motor 80 having a diaphragm 82.

Air admission means (not shown) control the admission and release of compressed air to the servo cylinder space 85 the base portion 86 of the servo motor 80 is forced upwardly away from the head portion 87. This displaces the beam 52 upwardly, to bring the jaw 54 into bite-forming relation with jaw 48.

An auxiliary jaw 58 carried at the outer toe end of each of the respective rib members 18, 43 provides contact with the respective beams 32, 52 to maintain substantial parallelism of the beams 32, 52 in relation to the rib members 18, 43 when the jaws are closed.

End abuttment plates 90 secured to the outer ends of the respective beams 32 and 52 in mutually vertically aligned relation ensure maintenance of accurate registry of the three other jaws 34, 48 and 54 with the master edge of the master jaw 28.

Actuation of the tester 10 is provided by way of an elongated tapered wedge bar 101 comprising an elongated bar slidably mounted in window 26 of the rib 18. An L-shaped section bearing shoe 103 is keyed into the window 26, to provide a right-angled support surface in which is seated the corner portion 105 of the wedge bar 101. The corner of the bar is relieved in order to permit a precise fit between bar 101 and bearing 103. A steady bearing 107 is held by adjustable cap screw 109 in pressing relation against a diagonal guide surface 115 of the bar 101.

The front vertical surface 117 of the bar 101 is slightly tapered so as to progressively fill the width of the window 26 as the bar 101 is advanced through the window.

A cam follower 119 having a spherical end abutting against the cam face 117 extends forwardly into abutting relation with a push rod 121 which is carried by the right hand assembly 44.

Thrust from the cam follower 119 through the push rod 121 to the assembly 44 is transmitted by way of a load measuring crystal 130 threadedly mounted within a window 126, to permit ready setting up by taking up lost motion of the actuator device.

In operation, with the wedge bar 101 retracted to an initial starting position, a paper web to be tested is mounted in the device.

Actuation of the wedge bar prime mover (not shown), to drive the wedge bar 101 into the window 26 causes the follower 119 to be displaced, so that the assembly 44 is displaced transversely away from the master jaw assembly 14 to produce rupture of the paper when a sufficient load, as read from the load measuring crystal has been supplied.

When testing for a zero-span condition, the clearance between the wedge bar 101 and the cam follower 119 will automatically disappear when the wedge bar 101 is set in motion. A force readout from the load measuring crystal will follow when all clearance has disappeared between wedge, follower and pushrod. A recorder (not shown) will indicate and if necessary record the straining load picked up from the crystal.

The wedge prime mover (not shown) is normally run at constant speed, in order to provide constant rate straining until breakage of the sample occurs. This produces values from which the much desired stress-strain curve can be obtained.

The above-noted prior art device utilising air loading effects substantially constant load straining, and cannot produce a stress-strain curve, because the rate at which the sample is stretched is not constant.

Comparison of the stress-strain curves obtained for short spans (spans having a value below maximum fibre-length) can prove both interesting and helpful.

For a given sheet, the stress-strain curve is the same when tested with a span greater than maximum fibre length.

Testing at other than under the so-called zero-span condition requires the wedge bar 101 to be initially advanced predetermined distances along the path of wedge travel, each such value of pre-travel representing an initial jaw separation of say 0.1, 0.2, 0.3, 0.5, 0.7, 1.0, 1.5mm etc. The wedge drive initial controls necessary to achieve repetitive station location in carrying out such pre-travel jaw separation does not constitute a part of the present invention.

After jaw pre-separation is effected a paper sample is clamped between both sets of jaws and strained until failure.

Jaw separation speed can be varied by controlling the rate of wedge displacement. Typically three wedge drive speeds may be provided, each selected drive speed being substantially constant in order to provide the generally desired constant rate straining.

Owing to the relatively great length of the pivot arm as defined by the distance between the test plane in which the paper lies, where it is gripped between the jaws, and the securing point under plate 47, in contrast to the very small distance of travel before bursting of the web occurs, the tensile force acting on the web can be considered as acting linearly.

It will be understood that the leaf spring 46 has a certain stiffness, which can be calibrated in relation to the bursting force, by displacing the moveable assembly 44 a distance equivalent to the degree of paper elongation at which rupture occurs. This produces a degree of flexure of the spring or plate 46 equal to that which will be achieved at bursting. In fact, the force registered by the load measuring crystal 130 will also include a value representing the force component necessary to displace the assembly 44 against gravitation pull. This component together with the plate bending force, represents a correction value to be subtracted from a web-burst value.

It would be evident that the plate 46 may be provided with an initial bending moment so as to apply a compressive load between jaw 48 and master jaw 28. The value of this bending moment, as it affects the load reading on the measuring crystal may be obtained in the same fashion as set forth above.

What I claim by Letters Patent of the United States is:

1. Testing apparatus for testing the tensile strength of a web of sheet material, having two pairs of clamping jaws in adjacent clamping relation for clamping adjoining portions of sheet material over a minimal zero gauge length, force applying wedge means to force one pair of jaws away from the other pair of jaws to cause rupture of the web, and force measuring means to measure the force required to rupture the web, one said pair of jaws comprising opposed first and second jaw portions, spring means extending between said first and second jaw portions to position them in mutual resiliently spaced relation, said spring means having substantially a single degree of freedom, to retain said jaws in predetermined self indexing relation.

2. Testing apparatus as claimed in claim 1, having positioning means to return one jaw of said pair into indexed relation with the jaw of the pair, and fluid inflatable expansion means located in direct load applying relation with one said jaw portion to provide closure thereof relative to the other jaw.

3. Testing apparatus as claimed in claim 2 including spacer means supporting said first and second jaw portions and said expansion means to provide reaction force between said jaws on inflation of said expansion means.

4. Testing apparatus as claimed in claim 1 having one said pair of jaws attached in pendant relation to said other pair of jaws.

5. Testing apparatus as claimed in claim 1 including axially displaceable wedge means located in force applying relation to force apart said two jaw sets, to rupture said web therebetween.

6. Testing apparatus as claimed in claim 5, said wedge means co-operating with force indicating means to give a reading of force applied by said wedge to said jaw sets.

* * * * *